(12) United States Patent
Richard et al.

(10) Patent No.: US 10,758,332 B2
(45) Date of Patent: Sep. 1, 2020

(54) PROSTHETIC REPAIR SYSTEM AND METHOD OF USE

(71) Applicant: C.R. Bard, Inc., Murray Hill, NJ (US)

(72) Inventors: Robert Richard, Wakefield, RI (US); Peter G. Davis, Dana Point, CA (US)

(73) Assignee: C.R. Bard, Inc., Murray Hill, NJ (US)

( * ) Notice: Subject to any disclaimer, the term of this patent is extended or adjusted under 35 U.S.C. 154(b) by 164 days.

(21) Appl. No.: 15/750,536

(22) PCT Filed: Aug. 8, 2016

(86) PCT No.: PCT/US2016/046010
§ 371 (c)(1),
(2) Date: Feb. 6, 2018

(87) PCT Pub. No.: WO2017/027461
PCT Pub. Date: Feb. 16, 2017

(65) Prior Publication Data
US 2018/0221127 A1 Aug. 9, 2018

Related U.S. Application Data

(60) Provisional application No. 62/204,823, filed on Aug. 12, 2015.

(51) Int. Cl.
*A61F 2/00* (2006.01)
*A61L 27/54* (2006.01)

(52) U.S. Cl.
CPC ............ *A61F 2/0063* (2013.01); *A61L 27/54* (2013.01); *A61F 2002/0072* (2013.01);
(Continued)

(58) Field of Classification Search
CPC ............ A61F 2002/0072; A61F 2/0063; A61F 2220/008; A61F 2250/0003;
(Continued)

(56) References Cited

U.S. PATENT DOCUMENTS

| 5,836,961 A | * | 11/1998 | Kieturakis | ......... A61B 17/0218 |
|---|---|---|---|---|
| | | | | 606/190 |
| 2007/0218101 A1 | * | 9/2007 | Johnson | ................. A61B 17/88 |
| | | | | 424/423 |

(Continued)

OTHER PUBLICATIONS

International Search Report and Written Opinion for International Application No. PCT/US2016/046010, dated Nov. 2, 2016.
International Preliminary Report on Patentability for International Application No. PCT/US2016/046010, dated Feb. 22, 2018.

*Primary Examiner* — Shaun L David
*Assistant Examiner* — Mohamed G Gabr
(74) *Attorney, Agent, or Firm* — Wolf, Greenfield & Sacks, P.C.

(57) ABSTRACT

A prosthetic repair system includes a prosthesis for repairing a defect in a tissue or muscle wall. A material delivery device is provided for delivering a material, such as an adhesive material, to a surface of the prosthesis and/or to particular locations between the prosthesis and the tissue or muscle wall to attach the prosthesis to the wall. The delivery device may be coupled to the prosthesis and configured to distribute the material from one side of the prosthesis to an opposite side that is to face the defect. The delivery device may include a manifold and conduits for delivering the material from the manifold to one or more desired locations. The conduits may penetrate into and/or through the thickness of the prosthesis. After delivery and distribution of the material, the delivery device may be removed from the prosthesis and withdrawn from) a patient.

15 Claims, 10 Drawing Sheets

(52) U.S. Cl.
CPC ........... *A61F 2220/0008* (2013.01); *A61F 2250/0003* (2013.01); *A61F 2250/0067* (2013.01); *A61L 2300/402* (2013.01); *A61L 2300/406* (2013.01); *A61L 2300/414* (2013.01); *A61L 2430/30* (2013.01); *A61L 2430/34* (2013.01)

(58) Field of Classification Search
CPC ....... A61F 2250/0067; A61B 17/00234; A61B 17/00491; A61B 17/0057; A61B 2017/00597; A61B 2017/00623; A61B 2017/00659; A61L 2300/402; A61L 2300/406; A61L 2300/414; A61L 2430/30; A61L 2430/34; A61L 27/54
See application file for complete search history.

(56) References Cited

U.S. PATENT DOCUMENTS

| | | | | |
|---|---|---|---|---|
| 2008/0065229 A1* | 3/2008 | Adams | ............... | A61F 2/0063 |
| | | | | 623/23.75 |
| 2009/0254103 A1* | 10/2009 | Deutsch | ............. | A61F 2/0063 |
| | | | | 606/151 |
| 2010/0282815 A1 | 11/2010 | Bettuchi et al. | | |
| 2010/0318121 A1* | 12/2010 | Levin | ............ | A61B 17/00491 |
| | | | | 606/213 |
| 2011/0213319 A1* | 9/2011 | Blott | ............... | A61M 3/0283 |
| | | | | 604/291 |
| 2011/0251566 A1* | 10/2011 | Zimnitsky | ............ | A61P 17/02 |
| | | | | 604/289 |
| 2013/0035704 A1 | 2/2013 | Dudai | | |

\* cited by examiner

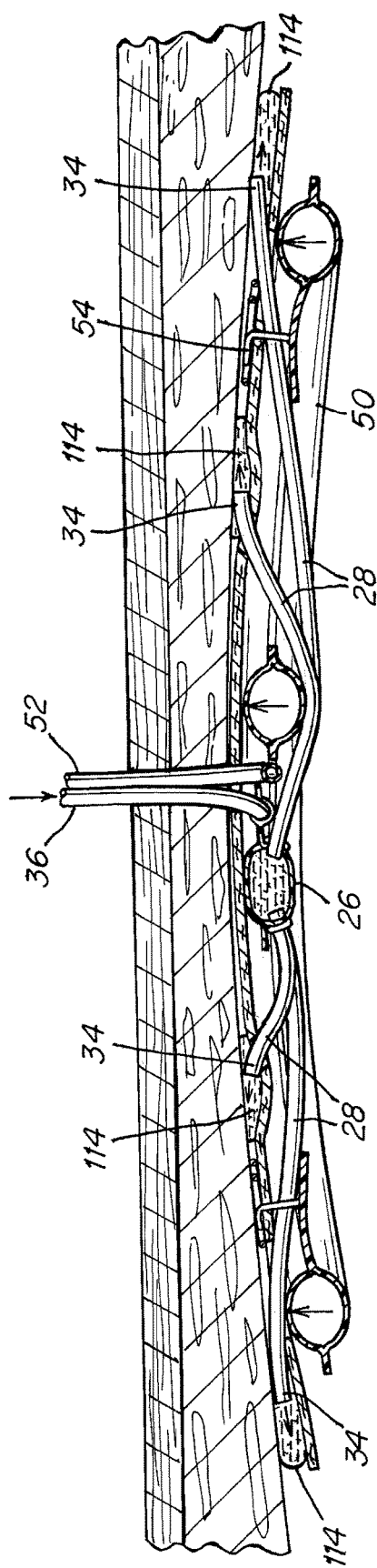
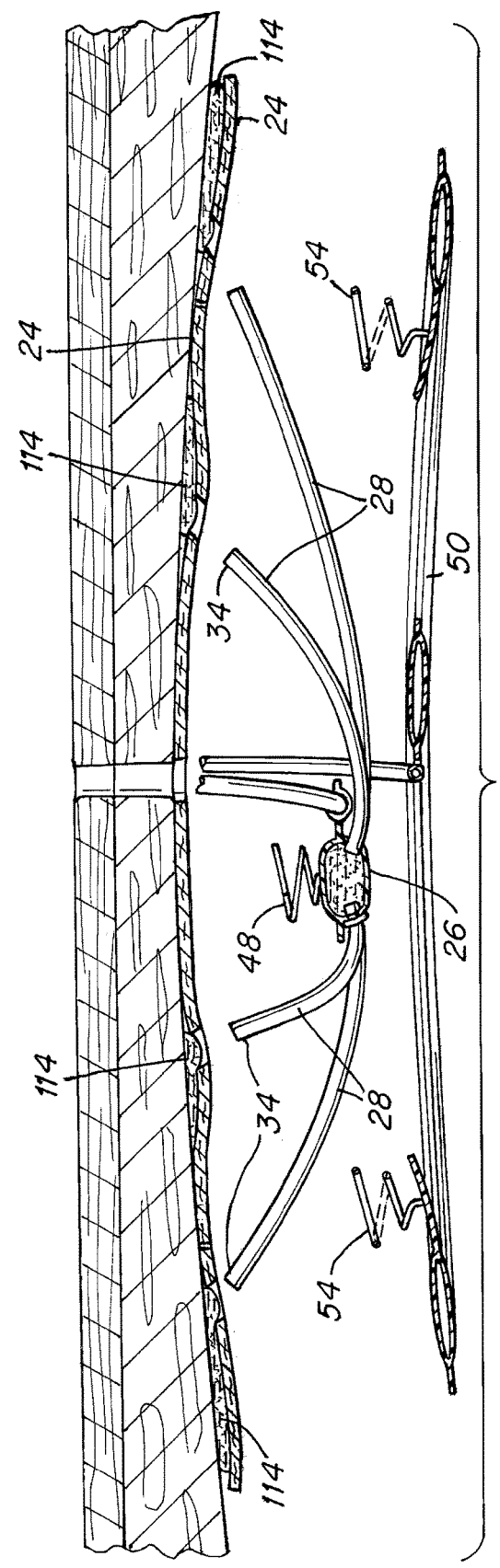

PROSTHETIC REPAIR SYSTEM AND METHOD OF USE

RELATED APPLICATIONS

This application is a 371 National Stage of International Patent Application No. PCT/US2016/046010, filed Aug. 8, 2016, which claims the benefit of U.S. Provisional Application No. 62/204,823, filed Aug. 13, 2015, the entire contents of which are incorporated herein by reference.

BACKGROUND

1. Field

The present invention relates to a prosthetic repair system, and more particularly, to a prosthetic repair system for repairing a defect in a tissue or muscle wall using a material delivery device.

2. Discussion of Related Art

Various prosthetic repair devices are known for repairing anatomical defects, such as soft tissue and muscle wall hernias. For example, ventral and inguinal hernias are commonly repaired using a sheet of biocompatible fabric, such as a knitted polypropylene mesh (e.g., BARD MESH). Once inserted into a patient, the fabric is typically sutured, stapled, tacked or otherwise provisionally anchored in place over, under or within the defect. Tissue integration with the fabric, such as by tissue ingrowth into the fabric, eventually completes the repair.

It is an object of the present invention to provide a prosthetic repair system for repairing soft tissue and muscle walls.

SUMMARY

Aspects of the present invention relate to a prosthetic repair system for repairing an anatomical defect, such as a tissue or muscle wall hernia, including a ventral hernia.

According to one aspect, a prosthetic repair system comprises an implantable prosthesis, such as a hernia repair patch, for repairing a defect in a tissue or muscle wall, and a material delivery device configured to be coupled to the prosthesis. The prosthesis includes first and second sides with a thickness therebetween. The material delivery device includes a manifold configured to be removably positioned adjacent the first side of the prosthesis and a plurality of delivery conduits fluidly coupled to the manifold. The manifold is configured to receive and distribute a material. Each of the plurality of delivery conduits includes an inlet to receive material from the manifold and an outlet to deliver the material to a location adjacent the second side of the prosthesis. Each of the plurality of delivery conduits is configured to penetrate through the entire thickness of the prosthesis with the outlet located at or protruding beyond the second side of the prosthesis.

According to another aspect, a prosthetic repair system comprises an implantable prosthesis for repairing a defect in a tissue or muscle wall, and a material delivery device configured to be coupled to the prosthesis. The prosthesis includes first and second sides with a thickness therebetween. The material delivery device includes a manifold configured to be removably positioned adjacent the first side of the prosthesis and configured to receive and distribute a material, and a plurality of delivery conduits fluidly coupled to the manifold to deliver the material between the second side of the prosthesis and the tissue or muscle wall when the prosthesis is positioned adjacent the tissue or muscle wall. Each of the plurality of delivery conduits is configured to be removable from the prosthesis.

According to a further aspect, a method is provided for repairing a defect in a tissue or muscle wall. The method comprises (a) introducing a prosthetic repair system into a patient, the prosthetic repair system including a prosthesis and a material delivery device coupled to the prosthesis. The prosthesis includes first and second sides with a thickness therebetween. The material delivery device includes a manifold positioned on the first side of the prosthesis and a plurality of conduits extending from the manifold into or through the thickness of the prosthesis. The method also comprises (b) positioning the prosthetic repair system at the defect with the first side of the prosthesis facing away from the defect in the tissue or muscle wall and the second side of the prosthesis facing toward the defect in the tissue or muscle wall; and (c) delivering material from the manifold to one or more locations between the second side of the prosthesis and the tissue or muscle wall via the plurality of conduits.

Various aspects of the present invention may provide certain advantages and may overcome certain drawbacks of prior repair devices. Aspects of the invention may not share the same advantages, and those that do may not share them under all circumstances.

BRIEF DESCRIPTION OF DRAWINGS

Various embodiments of the invention will now be described, by way of example, with reference to the accompanying drawings, in which:

FIGS. 6-12 are schematic views of a method of repairing a defect in a tissue or muscle wall using the prosthetic repair system of FIGS. 4-5 according to one illustrative embodiment, with FIGS. 10A and 10B being schematic cross-sectional views taken along section line 10-10 of FIG. 9;

DESCRIPTION

Figure 1:
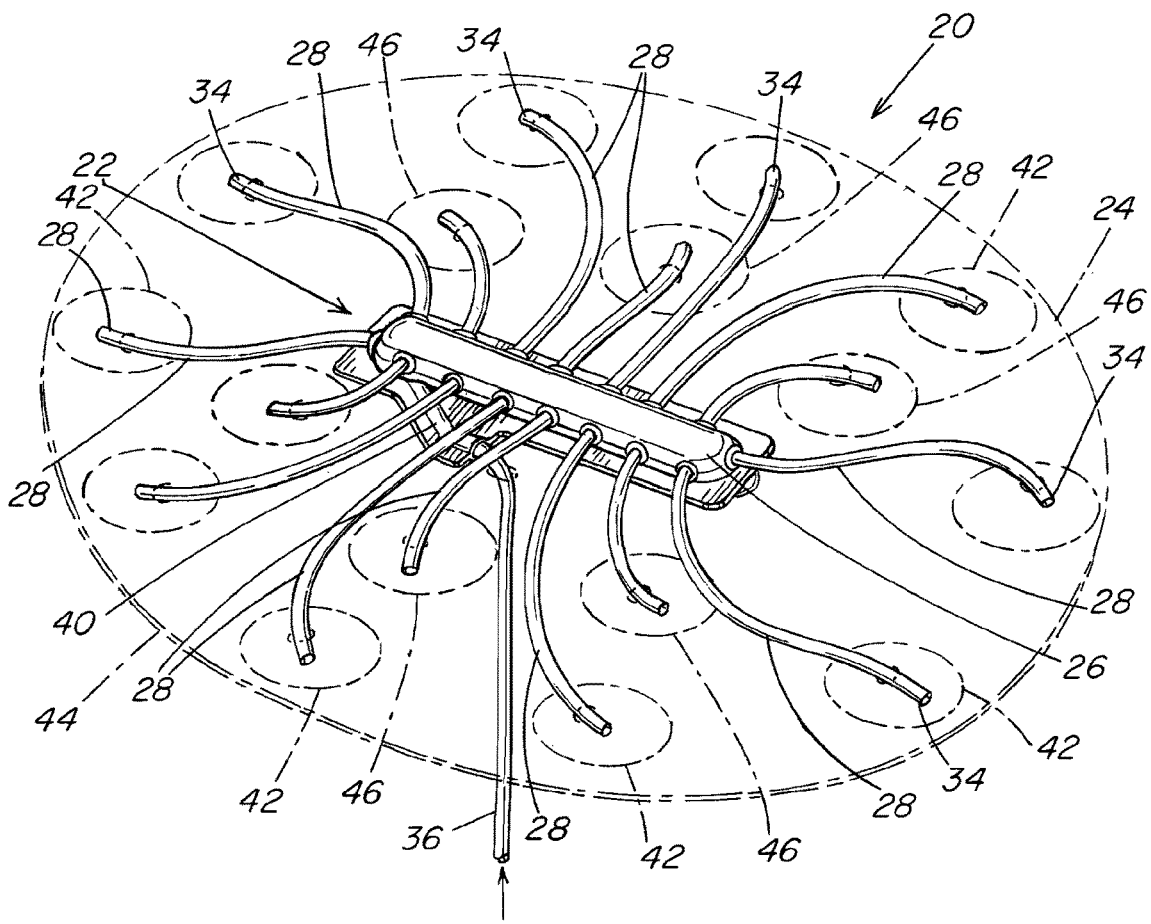
FIG. 1 is a perspective view of a prosthetic repair system for soft tissue or muscle wall repair according to one illustrative embodiment.

It should be understood that aspects of the invention are described herein with reference to the figures, which show illustrative embodiments in accordance with aspects of the invention. The illustrative embodiments described herein are not necessarily intended to show all aspects of the invention, but rather are used to describe one or more illustrative embodiments. Thus, aspects of the invention are not intended to be construed narrowly in view of the illustrative embodiments. It should be appreciated, then, that the various concepts and embodiments discussed herein may be implemented in any of numerous ways, as the disclosed concepts and embodiments are not limited to any particular manner of implementation. In addition, it should be understood that aspects of the invention may be used alone or in any suitable combination with other aspects of the invention.

Aspects of the invention are directed to a prosthetic repair system for repairing anatomical defects, and are particularly suitable for treating defects in soft tissue and muscle walls, such as the abdominal wall, or other anatomical regions. The repair system may include a prosthesis that promotes tissue or muscle ingrowth thereto and subsequently strengthens the area of the defect. The inventors have recognized that fixation of a prosthesis with fasteners or transfascial sutures that penetrate the tissue or muscle has been associated with post-surgical pain. Thus, the repair system may also include a material delivery device for delivering a fixation material, such as an adhesive or other material for cross-linking, catalyzing or activating an otherwise inactive material component provided on the prosthesis, to a surface of the prosthesis and/or to one or more locations between the prosthesis and the tissue or muscle wall to attach the prosthesis to the tissue or muscle wall. Additionally or alternatively, the material delivery device may be employed to deliver other materials, such as antibiotics, analgesics, growth factors and other therapeutic materials, as should be apparent to one of skill in the art.

The material delivery device may be coupled to a first side of the prosthesis, such as the posterior side, that is to be positioned facing away from the defect in the tissue or muscle wall. The delivery device may be configured to distribute the material from the first side of the prosthesis to a second side of the prosthesis, such as the anterior side, that is to be positioned facing the defect in the tissue or muscle wall. If desired, the delivery device may be coupled to a side of the prosthesis that is to be positioned facing the defect. The delivery device may be configured to distribute the material to one or more desired locations and/or in one or more defined patterns, for example, to optimize fixation of the prosthesis to the tissue or muscle wall while also maximizing the potential for tissue ingrowth.

After delivery and distribution of the material, the material delivery device may be removed from the prosthesis and withdrawn from a patient. Removal of the material delivery device may occur after the prosthesis has become attached to the tissue or muscle wall. However, removal of the material delivery device, if desired, may occur at any suitable time as should be apparent to one of skill. It is contemplated that the material delivery device may be configured to remain with the prosthesis after delivery of the material. It is also contemplated that the material delivery device, or one or more portions thereof, may be formed of resorbable or absorbable material.

The material delivery device may include a manifold that is removably positioned adjacent the first side of the prosthesis. The manifold is configured to distribute a material, such as an adhesive material, for attaching the prosthesis to the tissue or muscle wall. An inlet conduit may be provided to deliver material to the manifold for subsequent distribution. The inlet conduit may be arranged to extend through the prosthesis and tissue or muscle wall with sufficient length to be accessible from outside a patient. In this manner, material may be introduced from outside a patient to the manifold after placement of the prosthetic repair system within the patient. Alternatively, the inlet conduit may extend through an opening or a laparoscopic cannula. In some embodiments, a manifold may be preloaded with material and an inlet conduit may not be required.

A plurality of delivery conduits may be fluidly coupled to the manifold for delivering the material to a surface of the prosthesis and/or between the prosthesis and the tissue or muscle wall. In some embodiments, one or more of the delivery conduits may penetrate through some of the thickness of the prosthesis, or through all of the thickness and to a particular location adjacent the second side of the prosthesis where it is desired to deliver material. In some embodiments, one or more of the delivery conduits may be removed from the prosthesis, for example, along with the manifold, following delivery of the material.

In some embodiments, the delivery conduits may include elongated tubes that extend from the manifold to a desired location of the prosthesis for delivery of material at the desired locations. In some embodiments, the delivery conduits may include projections, such as nipples, which project from the manifold in a desired arrangement to penetrate the prosthesis at desired locations.

The manifold and/or conduits may be flexible or otherwise collapsible so that the prosthetic repair system may be reduced in size to facilitate delivery of the repair device to the treatment site, for example, using a minimally invasive technique or certain open procedures. For example, in a laparoscopic procedure, a hernia repair prosthesis, such as a patch, may be rolled into a slender cylindrical shape, or otherwise collapsed into a smaller configuration, suitable for passage through a narrow cannula which may have an inner diameter of approximately 10 mm, of approximately 5 mm, or even a finer size.

To assist in unfurling the prosthetic repair system into an expanded shape after deployment through a cannula, a support member may be coupled to the prosthesis. The support member may include an inflatable device, such as a balloon, that can be inflated after deployment to expand the prosthetic repair system. When deflated, the support member may be rolled or otherwise collapsed into a reduced configuration along with the prosthesis and/or the material delivery device for delivery through the laparoscopic cannula to the hernia repair site. An inflation tube may be provided to inflate the support member. The inflation tube may be arranged to extend through the prosthesis and tissue or muscle wall with sufficient length to be accessible from outside a patient. The support member may be attached to the prosthesis in a manner that permits the support member to be removed from the prosthesis and withdrawn from the patient.

Alternatively, or additionally, the support member may have a resiliency or other property (e.g., shape memory) that allows the support member to deform from an initial, expanded, shape into a compact configuration as the patch is reduced in size for laparoscopic delivery, and then return to the initial shape, or at least to a shape larger than the reduced shape, upon exiting the cannula. Recovery of the support member causes the attached patch to spread out into an expanded configuration. For example, and without limitation, the support member may be rollable into a reduced size for delivery through the laparoscopic cannula to the defect repair site. A representative support member may be formed from a NITINOL wire. The support member may have a frame-like shape and may generally follow the periphery of the patch. Representative shapes of a support member include circular, oval or a polygon. It is to be appreciated that the support member may be formed of any suitable material and have any desired configuration as should be apparent to one of skill in the art.

In some embodiments, the material delivery device and the support member may be separate devices attachable to and removable from the prosthesis. In some embodiments, the material delivery device may be integrated with the support member as a single component.

After deployment through the laparoscopic cannula, and unfurling of the support member, the expanded prosthesis may be located against the abdominal wall and fixated in place using material delivered to the surface of the prosthesis and/or to one or more locations between the prosthesis and the abdominal wall with the material delivery device. With the prosthesis spread out over the defect, and secured to the tissue or muscle wall, the inventors have recognized that there no longer is a need for the support member. Accordingly, the support member may be releasably attached to the prosthesis, allowing selective removal of the support member by the surgical team after expanding, positioning, and/or fixation of the patch body.

For ease of understanding, and without limiting the scope of the invention, the prosthetic repair system is described below particularly in connection with the repair of a ventral hernia. It should be understood, however, that the repair system is not so limited and may be employed in other anatomical procedures, as should be apparent to one of skill in the art. For example, and without limitation, the repair system may be employed for chest or abdominal wall reconstruction, or large defects, such as those that may occur in obese patients. The repair system may include one or more features, each independently or in combination, contributing to such attributes.

Figure 2:
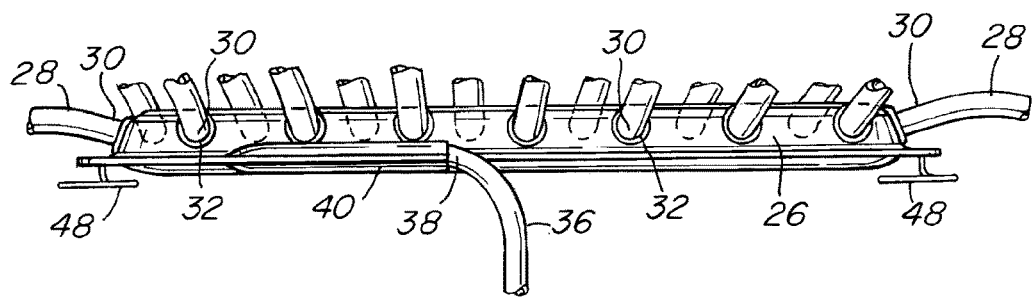
FIG. 2 is a side view of the prosthetic repair system of FIG. 1.
Figure 3:
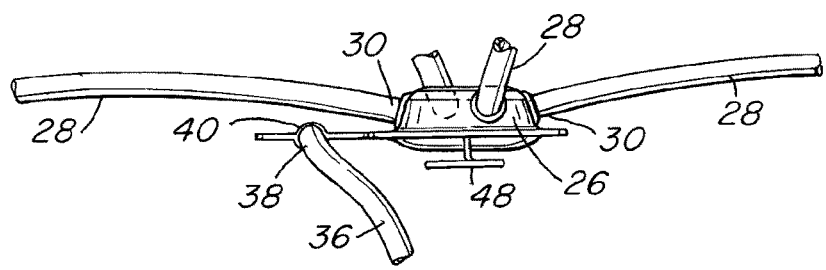
FIG. 3 is an end view of the prosthetic repair system of FIG. 1.

In one illustrative embodiment shown in FIGS. 1-3, a prosthetic repair system 20 includes a material delivery device 22 that is attachable to an implantable prosthesis 24 (shown in phantom). The material delivery device may include a manifold 26 for distributing a material through one or more output or delivery conduits 28 fluidly coupled to the manifold. An inlet 30 of a delivery conduit 28, which may be provided at a first end thereof, may be coupled to an outlet 32 of the manifold 26. Material from the manifold passes along the delivery conduit exiting from an outlet 34, which may be provided at a second end thereof. A delivery conduit 28 may be configured to penetrate and extend partially through the prosthesis, or completely through the prosthesis, so that material may be delivered to a side of the prosthesis opposite to the location of the manifold.

To introduce material into the manifold, the material delivery device 22 may include an input conduit 36 fluidly coupled to the manifold 26. An outlet 38 of the input conduit 36, which may be provided at a first end thereof, may be coupled to an inlet 40 of the manifold. Material introduced at the inlet, which may be provided at the second end thereof, passes along the input conduit to the manifold. As shown, the input conduit may be configured to penetrate and extend through the prosthesis 24 and have a length sufficient to be externally accessible from outside a patient when the prosthetic repair system is located at a repair site within the patient. In this manner, material may be introduced into the manifold from outside the patient after the repair system has been placed in the patient.

It is to be appreciated that the input conduit is not required to pass through the prosthesis for each embodiment of the prosthetic repair system. For example, and without limitation, the input conduit may extend or run along the same side or surface of the prosthesis as the manifold before passing to an external location outside the patient.

The manifold 26 may include any number of inlets, outlets and conduits, which may be provided at any desired location. In one embodiment, the outlets and delivery conduits are spaced about the periphery of the manifold. As shown, outlets and delivery conduits may be provided at each end of the manifold as well as along the sides. The manifold inlet and input conduit may be coupled to a side of the manifold. However, the manifold may employ any suitable arrangement of outlets, inlets and/or conduits as should be apparent to one of skill.

The delivery conduits 28 may be arranged to deliver material in any desired pattern relative to the prosthesis. In one embodiment shown in FIG. 1, the delivery conduits 28 may be arranged to deliver material to outer regions 42 adjacent the outer periphery 44 of the prosthesis as well as to inner regions 46 located between the outer regions 42 and the manifold 26. This may be accomplished by varying the lengths of the individual conduits 28 relative to its manifold outlet 32 and the particular region for material delivery. For example, relatively longer conduits may be used for delivering material to the outer regions and relatively shorter conduits may be used for delivering material to the inner regions.

It is to be appreciated that other arrangements are contemplated for distributing material in any desired pattern or to any desired regions. For example, and without limitation, the material delivery device may employ a manifold configured to overlie portions of the prosthesis where it is desired to deliver material with the delivery conduits extending from a surface of the manifold that faces the prosthesis and arranged in a pattern corresponding to the desired regions of material delivery.

The manifold 26 and/or conduits 28, 36 may be flexible or otherwise collapsible so that the prosthetic repair system may be reduced in size to facilitate delivery of the repair system to the treatment site, for example, using a minimally invasive technique or certain open procedures. The manifold and conduits may be formed from a variety of materials, as the invention is not limited in this respect. In one embodiment, the manifold 26 may be formed of polyurethane, and may, for example, be formed of nylon coated polyurethane. In one embodiment, the manifold may be formed of two layers of nylon coated polyurethane that together form an expandable manifold chamber for the introduction and delivery of material.

The conduits 28, 36 may be formed from a resilient or flexible tube material, such as a plastic or elastomer, which allows the conduits to be folded and/or collapsed without creating a permanent pinch or fold when the conduits are subsequently returned to an expanded or unfolded configuration. The conduits 28, 36 may be coupled to the manifold using any suitable arrangement as should be apparent to one of skill. For example, and without limitation, the conduits may be press-fit, threaded or bonded to the outlets. In some embodiments, the conduits may be integrally formed with the manifold.

The manifold 26 may be configured to be removably coupled to the prosthesis so that the material delivery device may be removed from the prosthesis after implantation of the prosthesis and/or delivery of the material. The manifold may include one or more fasteners 48 that are configured to releasably attach the manifold to the prosthesis. In one embodiment, a fastener 48 may include a resilient coil that can be threaded through the prosthesis to attach the manifold 26 and can be readily pulled or stripped from the prosthesis to detach the manifold. As shown, the coil 48 may have a flat configuration to provide a thin construction for rolling or otherwise collapsing the prosthetic repair system for delivery into a patient. However, it is to be appreciated that the manifold may employ fasteners having any suitable configuration as should be apparent to one of skill in the art.

In some embodiments, it is contemplated that the manifold and/or conduits, or one or more portions thereof, may be formed of resorbable or absorbable material.

The prosthesis may be placed at the defect site using an open surgical procedure or a minimally invasive procedure, such as by laparoscopically passing the device through a cannula to the defect. The repair fabric may be flexible, allowing reduction of the prosthesis, such as by folding, rolling or otherwise collapsing the repair fabric, into a slender configuration suitable for delivery to the defect site. Upon delivery, the repair fabric may automatically open to an unfurled or spread out configuration, or may be unfolded, unrolled or otherwise deployed by the surgeon to an unfurled or spread out configuration suitable to repair the weakness or defect.

For some embodiments, it may be desirable for the prosthetic repair system 20 to employ a support member to assist in unfurling a rolled, folded up or otherwise reduced prosthesis into an expanded shape after deployment, such as through either a cannula or an open incision, at the treatment site. The support member facilitates deployment and placement of the prosthesis by making it easy to handle. The support member also minimizes the tendency of the prosthesis to fold, bend, or otherwise be dislocated. Difficulty in handling, dislocation or bending could require additional operative procedures and/or additional anchoring during implantation.

Figure 4:
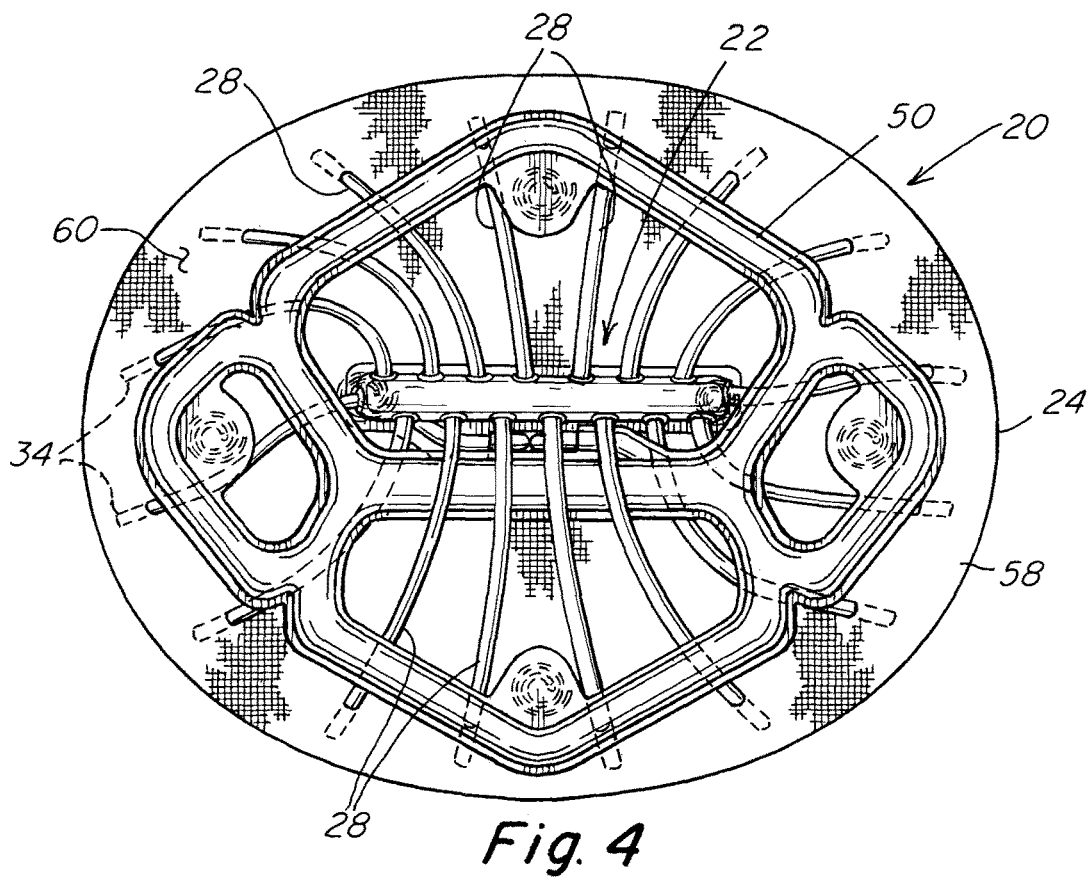
FIG. 4 is a posterior side view of a prosthetic repair system for soft tissue or muscle wall repair according to another illustrative embodiment.
Figure 5:
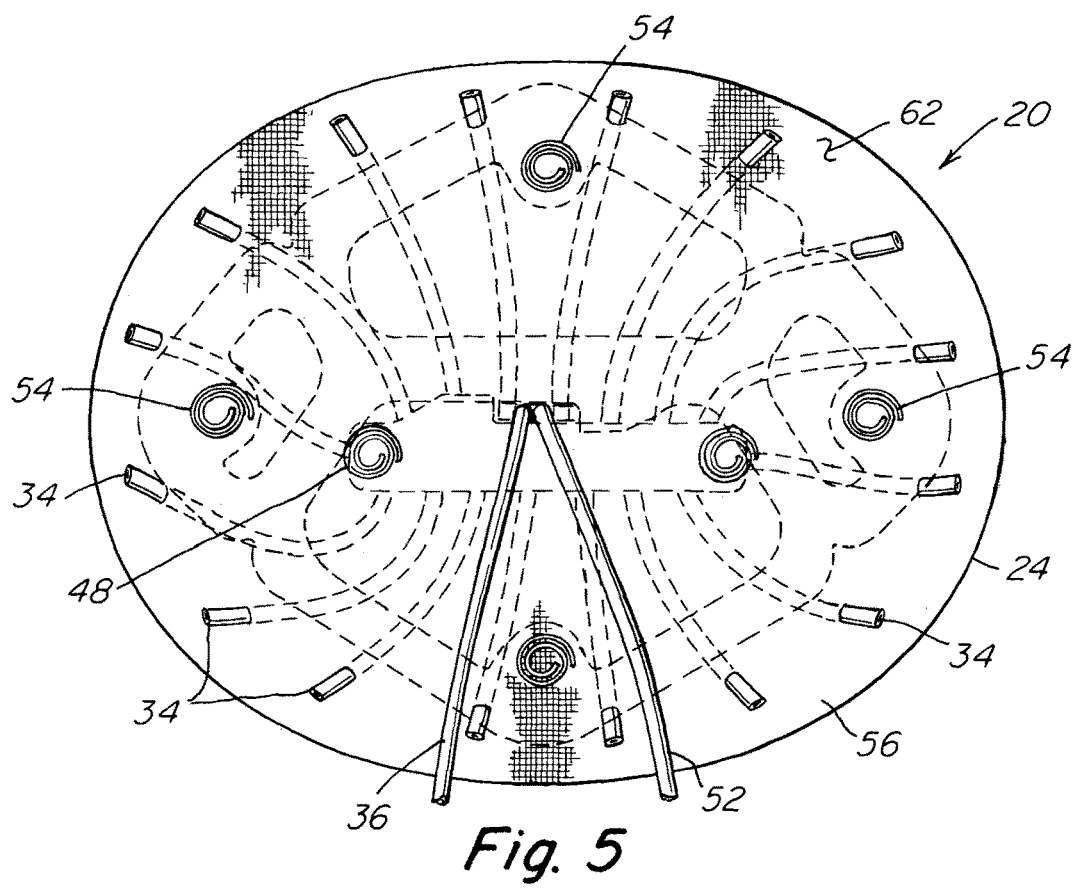
FIG. 5 is an anterior side view of the prosthetic repair system of FIG. 4.

In one illustrative embodiment shown in FIGS. 4-5, the prosthetic repair system includes a support member 50 that may be positioned adjacent the same side of the prosthesis 24, such as the posterior side, as the manifold 26. In one embodiment, the material delivery device and the support member may be separate devices attached to the prosthesis. In some embodiments, the material delivery device may be integrated with the support member.

In one embodiment, the support member 50 may include an inflatable device, such as a balloon, that can be inflated after deployment to expand the prosthetic repair system. As illustrated, the support member may include various elongated members that are coupled in fluid communication with each other to form a single inflatable bladder. However, it is to be appreciated that the support member may employ any suitable configuration as should be apparent to one of skill.

When deflated, the support member 50 may be rolled or otherwise collapsed into a reduced configuration along with the prosthesis 24 and/or the material delivery device 22 for delivery through the laparoscopic cannula to the hernia repair site. An inflation tube 52 may be provided to inflate the support member. The inflation tube 52 may be arranged to extend through the prosthesis 24 and tissue or muscle wall with sufficient length to be accessible from outside a patient.

For embodiments in which the material delivery device is integrated with the support member, it may be desirable to integrate the input conduit 36 of the material delivery device 22 and the inflation tube 52 of the support member 50 in a single structure. For example, and without limitation, a dual lumen tube or conduit may be employed with the repair system in which the input conduit 36 corresponds to a first lumen and the inflation tube 52 corresponds to a second lumen.

The support member 50 may be attached to the prosthesis in a manner that permits the support member to be removed from the prosthesis and withdrawn from the patient. The support member may include one or more fasteners 54 that are configured to releasably attach the support member to the prosthesis. Similar to the manifold attachment arrangement described above, a fastener 54 may include a resilient coil, which may have a flat configuration, that can be threaded through the prosthesis 24 to attach the support member 50 and can be readily pulled or stripped from the prosthesis to detach the support member. However, it is to be appreciated that the support member may employ fasteners having any suitable configuration that permits removal of the support member as should be apparent to one of skill in the art.

One example of a support member 50, as shown in the illustrative embodiment, that may be particularly suitable for use with the prosthetic repair system, is the ECHO PS Positioning System, available from C.R. Bard, Inc. However, it is to be appreciated that the repair system may employ other support members having any suitable configuration as should be apparent to one of skill in the art. For example, and without limitation, the support member may have a resiliency or other property (e.g., shape memory) that allows the support member to deform from an initial, expanded shape into a compact configuration as the patch is reduced in size for laparoscopic delivery, and then return to the initial shape, or at least to a shape larger than the reduced shape, upon exiting a cannula. Recovery of the support member causes the attached prosthesis to spread out into an expanded configuration. For example, and without limitation, the support member may be rollable into a reduced size for delivery through the laparoscopic cannula to the hernia repair site.

A support member may be formed from a shape memory wire, such as NITINOL. The support member may have a frame-like shape and may generally follow the periphery of the prosthesis.

Another example of a support member is a monofilament that has been preformed into the desired shape or may be placed into the desired shape during assembly of the prosthesis. The support member may be comprised of a non-absorbable or non-resorbable material or an absorbable or resorbable material.

As shown, the delivery conduits 28 may be positioned to extend between the prosthesis 24 and portions of the support member 50. This arrangement may assist with retaining the delivery conduits in position on the prosthesis. However, it is to be appreciated that such an arrangement is not required for each embodiment of the prosthetic repair system.

The prosthetic repair system may employ a prosthesis 24 including a repair fabric having a body portion that is configured to cover or extend across the defect opening or weakness when the body portion is placed against the defect. In one illustrative embodiment shown in FIGS. 4-5, the prosthesis 24 may be in the form of a patch, although the prosthesis may employ other configurations as should be apparent to one of skill in the art. For example, and without limitation, the prosthesis may include a plug, a combination plug and patch, and other suitable arrangements for repairing the defect.

As shown, the prosthesis 24 may have a non-circular shape, such as a generally oval, elliptical or egg shape, that is suitable for repairing a tissue or muscle wall defect, such as a hernia defect. However, the prosthesis may employ any suitable shape including, but not limited to, circular or rectangular shapes, as should be apparent to one of skill in the art.

The prosthesis 24 may include a patch body having a surface 56, such as an anterior surface, that is arranged for tissue ingrowth and an opposite surface 58, such as a posterior surface, that is configured as an adhesion resistant barrier between the anterior surface 56 and sensitive organs or tissue, such as the intestines or other viscera. The anterior surface 56 may include a tissue infiltratable layer such as a mesh or other porous fabric amenable to tissue ingrowth, and the posterior surface 58 may be a solid or substantially non-porous barrier layer or a barrier coating that will prevent contact between the viscera and the porous tissue ingrowth fabric and resist tissue ingrowth. Alternative arrangements of a patch body are contemplated as should be apparent to one of skill in the art. For example, and without limitation, the patch body may include only a tissue infiltratable layer, only a solid or non-tissue infiltratable layer, or a combination of tissue infiltratable and non-tissue infiltratable aspects situated in the same layer.

The patch body may be formed of a porous material, such as a knit fabric, woven or non-woven fabric, or may be composed of a solid, substantially non-porous, or microporous material. The patch body may be formed of one or more layers of the same or dissimilar material, and the layers may be stacked one on top of the other, side-to-side, or include a combination of both stacking arrangements. The patch body may be formed with portions that are tissue infiltratable and other portions that are less tissue infiltratable or are non-tissue infiltratable, providing selected areas of the repair device with different tissue ingrowth and adhesion resistant properties. The patch body may be formed of permanent material, absorbable or resorbable material, or a combination of permanent and absorbable or resorbable materials. It should be appreciated that the patch body may be formed of any biologically compatible material, synthetic or natural, suitable for repairing a tissue or muscle wall defect as should be apparent to one of skill in the art.

In one illustrative embodiment of FIGS. 4-5, the prosthesis 24 is configured as a patch that includes a tissue infiltratable layer 60 and a barrier layer 62. The tissue infiltratable layer may include one or more sheets of surgical mesh fabric, such as a polypropylene knit. The barrier layer may be a sheet of synthetic or natural barrier material; for example, and without limitation, a sheet of ePTFE may be stitched, heat fused or otherwise connected to a polypropylene sheet. Another option is to embed the polypropylene knit into a film of SEPRA (bioresorbable hydrogel barrier). Such an arrangement may be particularly suited for repairing a ventral hernia where the polypropylene side would face the abdominal wall and the ePTFE or SEPRA side would face the viscera.

As illustrated in FIG. 4, a material delivery device 22 and an inflatable support member 50 may be coupled to the patch adjacent the barrier layer 62 on one side of the patch. The delivery conduits 28 extend from the manifold 26 and through the entire thickness of the patch with the outlets 34 of the delivery conduits protruding beyond the tissue infiltratable layer 60 on the other side of the patch, as shown in FIG. 5. The outlets of the delivery conduits may be located about and proximate to the outer periphery of the patch. The delivery tube 36 of the material delivery device and the inflation tube 52 of the support member may extend through a central region of the patch. However, any arrangement of delivery conduits, delivery tube and/or inflation tube may be implemented with the prosthetic repair system as should be apparent to one of skill in the art.

As indicated above, the prosthetic repair system may be employed to repair various tissue or muscle wall defects, such a hernia defects. The prosthetic repair system illustrated in FIGS. 4-5 may be particularly suited for repairing a ventral hernia. A representative procedure for using this repair system is now described in conjunction with FIGS. 6-12.

Figure 6:
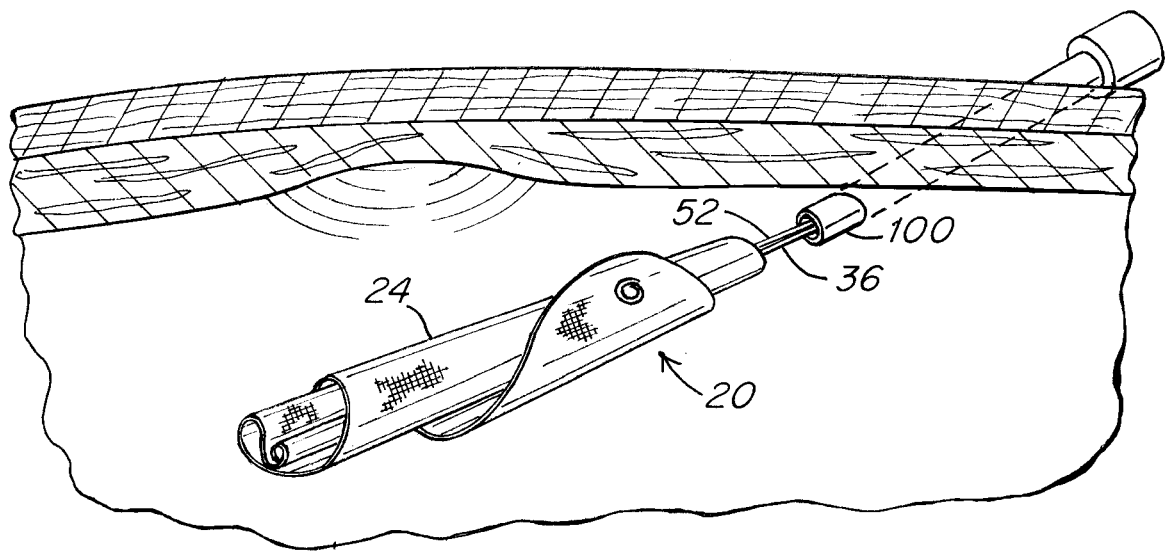

As shown in FIG. 6, a prosthetic patch 24 is rolled along an axis thereof into a small configuration, and then delivered through a narrow incision or cannula 100 into the abdominal cavity of a patient. The patch may be rolled using an introducer tool (not shown) with the material delivery device 22 and the support member 50 being located on the inside of the rolled patch.

Figure 7:
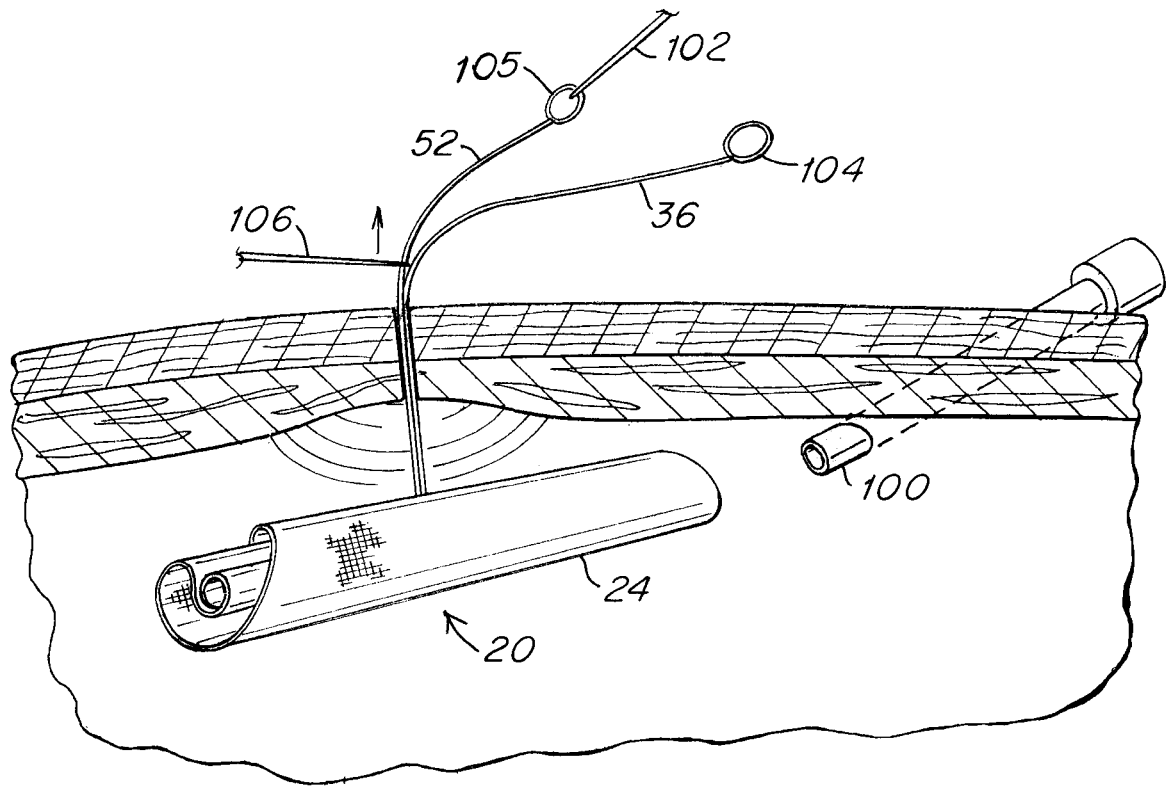

After being delivered into the abdominal cavity, each of the input conduit 36 and the inflation tube 52 may be located using a grasper or other surgical tool. As shown in FIG. 7, the input conduit 36 and the inflation tube 52 may be retrieved and pulled through the abdominal wall, such as through the hernia defect, by grasping a retrieval loop 104, 105 provided on each of the input conduit and the inflation tube. A suture passer device 102 or other suitable tool may be employed to retrieve and pull the input conduit and the inflation tube through the abdominal wall to a location outside the patient.

The input conduit 36 and the inflation tube 52 may be configured to allow a user to distinguish between them using any suitable arrangement or scheme as should be apparent to one of skill. For example, and without limitation, the input conduit 36 and the inflation tube 52 and/or the retrieval loops 104, 105 associated with them may have different colors, such as red for the input conduit and blue for the inflation tube.

An atraumatic clamp or hemostat 106 may be placed on the inflation tube 52 at the level of the skin to temporarily hold the repair device in position within the abdominal cavity. The inflation tube may be cut and the retrieval loop discarded.

Figure 8:
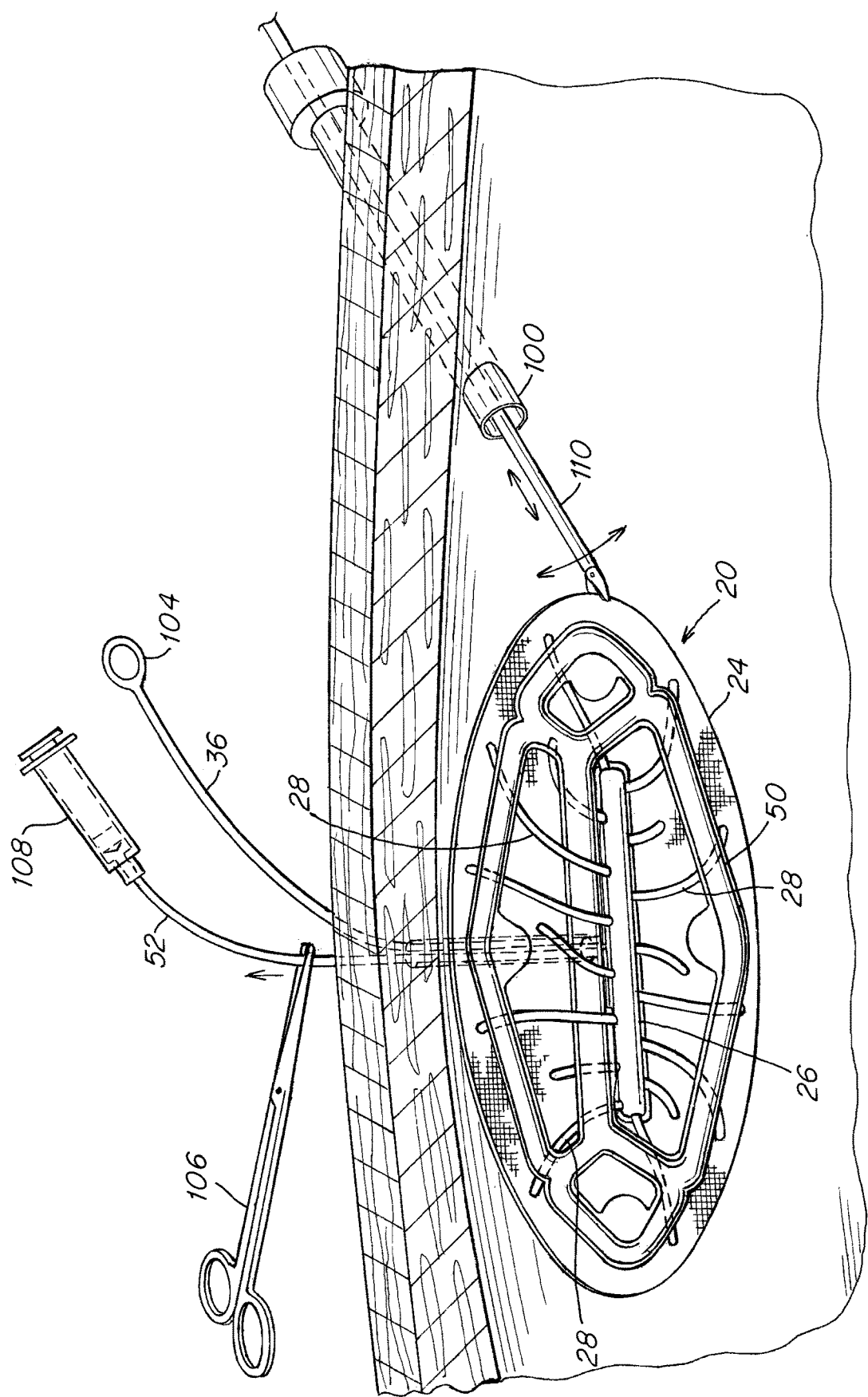

To inflate the support member, the clamp or hemostat 106 is released and the inflation tube 52 is pulled upward to lift the prosthesis 24 away from the viscera, as shown in FIGS. 7 and 8. A syringe 108 or other suitable device is attached to the inflation tube 52 and pumped until the support member 50 is fully inflated, as shown in FIG. 8. The inflation tube 52 may be clamped to maintain inflation of the support member and the syringe removed. The prosthesis may then be oriented in relation to the defect using a grasper 110 or other suitable tool.

Figure 9:
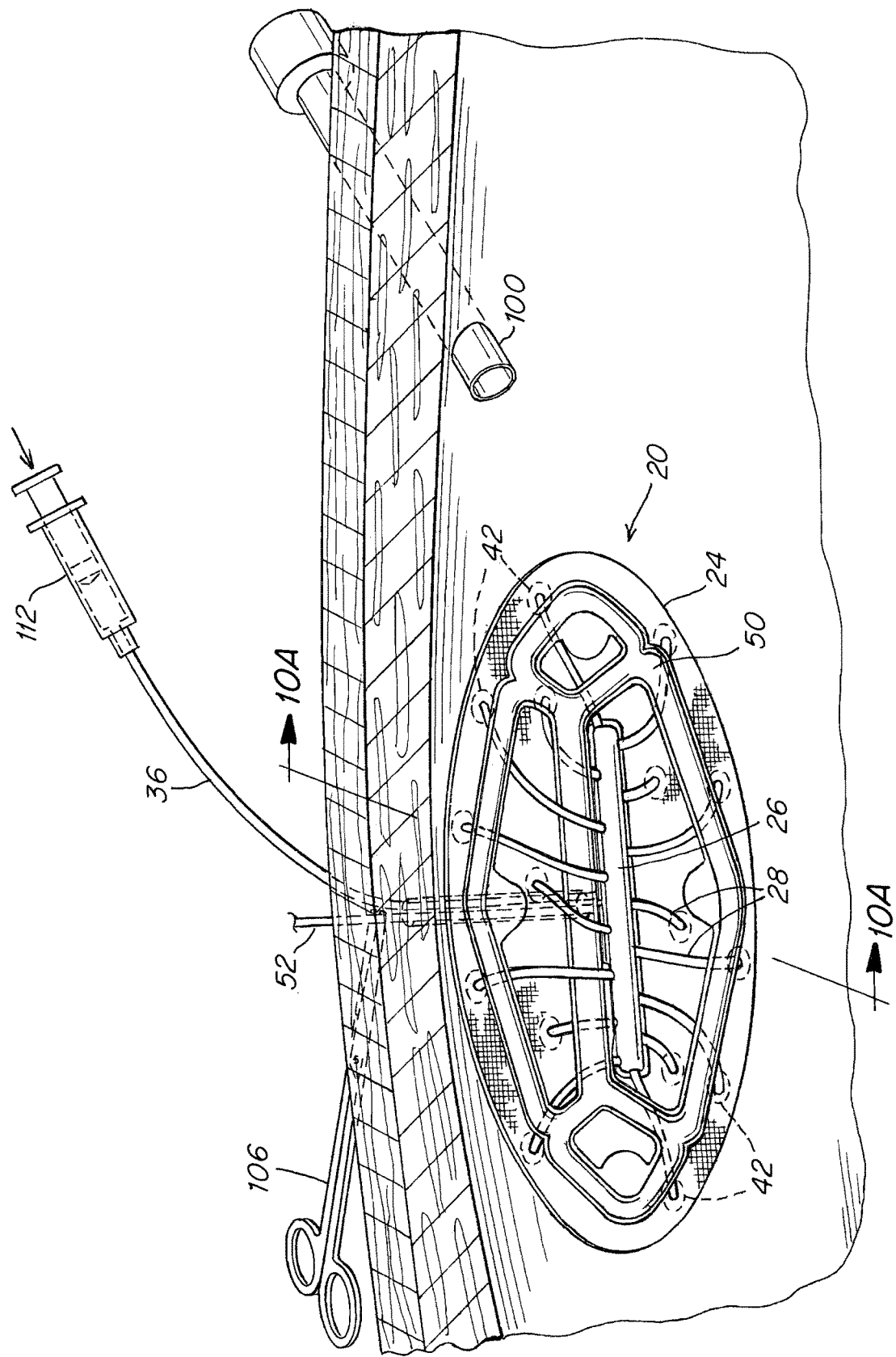

Once the prosthesis has been positioned and prior to deflation of the support member 50, the prosthesis is fixed in position. This may be accomplished using an adhesive or other material that is introduced between the prosthesis and the abdominal wall. As shown in FIG. 9, after removing the retrieval loop 104, a material dispenser 112 is attached to the material delivery tube 36 and is actuated to deliver, such as by injecting, adhesive material to the manifold. The adhesive material 114 then flows through the manifold for distribution to the manifold outlets. Material then passes along the delivery conduits 28 extending through the prosthesis delivery conduits for delivery to one or more attachment regions between the prosthesis and the abdominal wall, as shown in FIG. 10A.

After the prosthesis is secured in position using the adhesive material 114, the support member 50 may be deflated by releasing the clamp 106 on the inflation tube 52.

The inflation tube 52 and/or the input conduit 36 may be cut, preferably as close to the skin as possible, and discarded.

Figure 11:
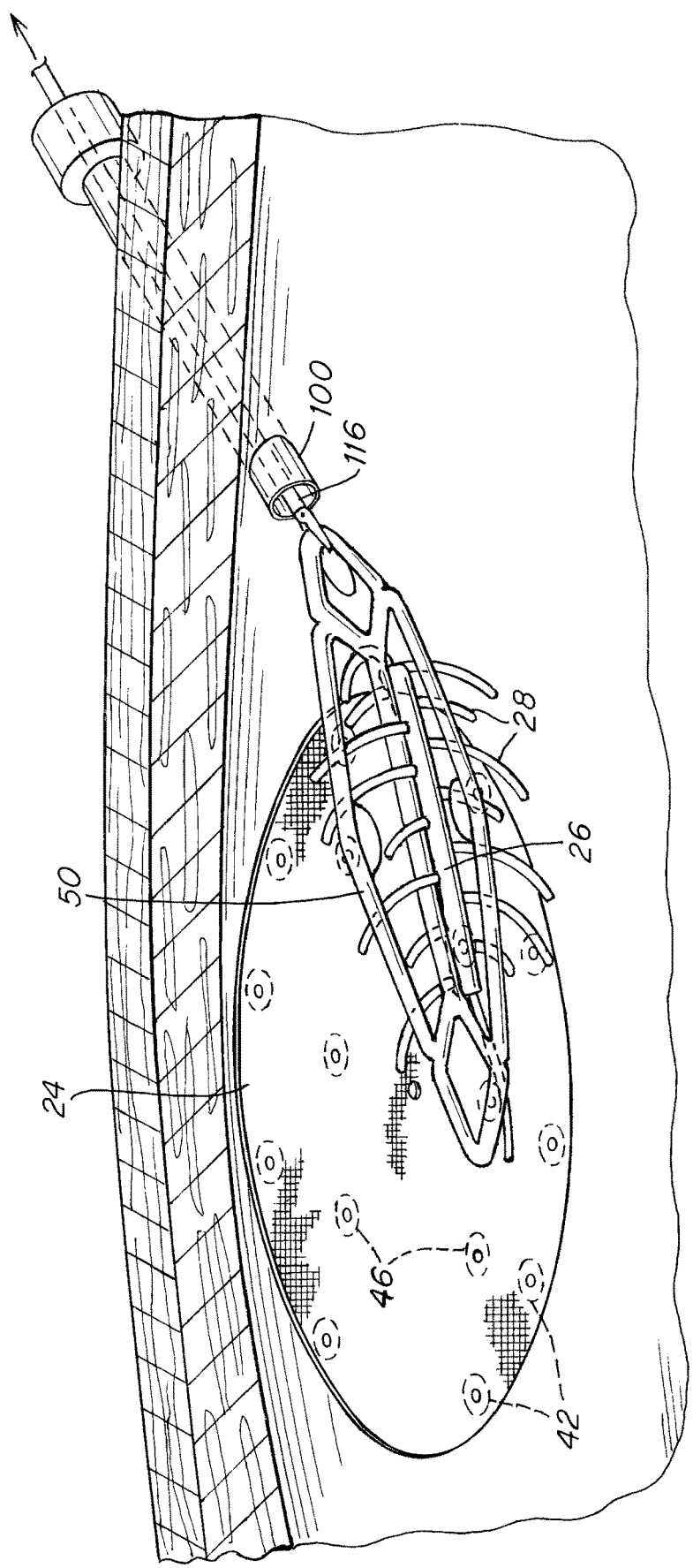

As shown in FIGS. 10B and 11, the deflated support member 50 and the material delivery device 22 may be pulled and removed from the prosthetic patch 24 using a grasper 116 or other suitable instruments. The support member 50 and the material delivery device 22, including the manifold 26, the delivery conduits 28 and the material delivery tube 36, may be withdrawn from the abdominal cavity through the cannula and/or puncture.

Figure 12:
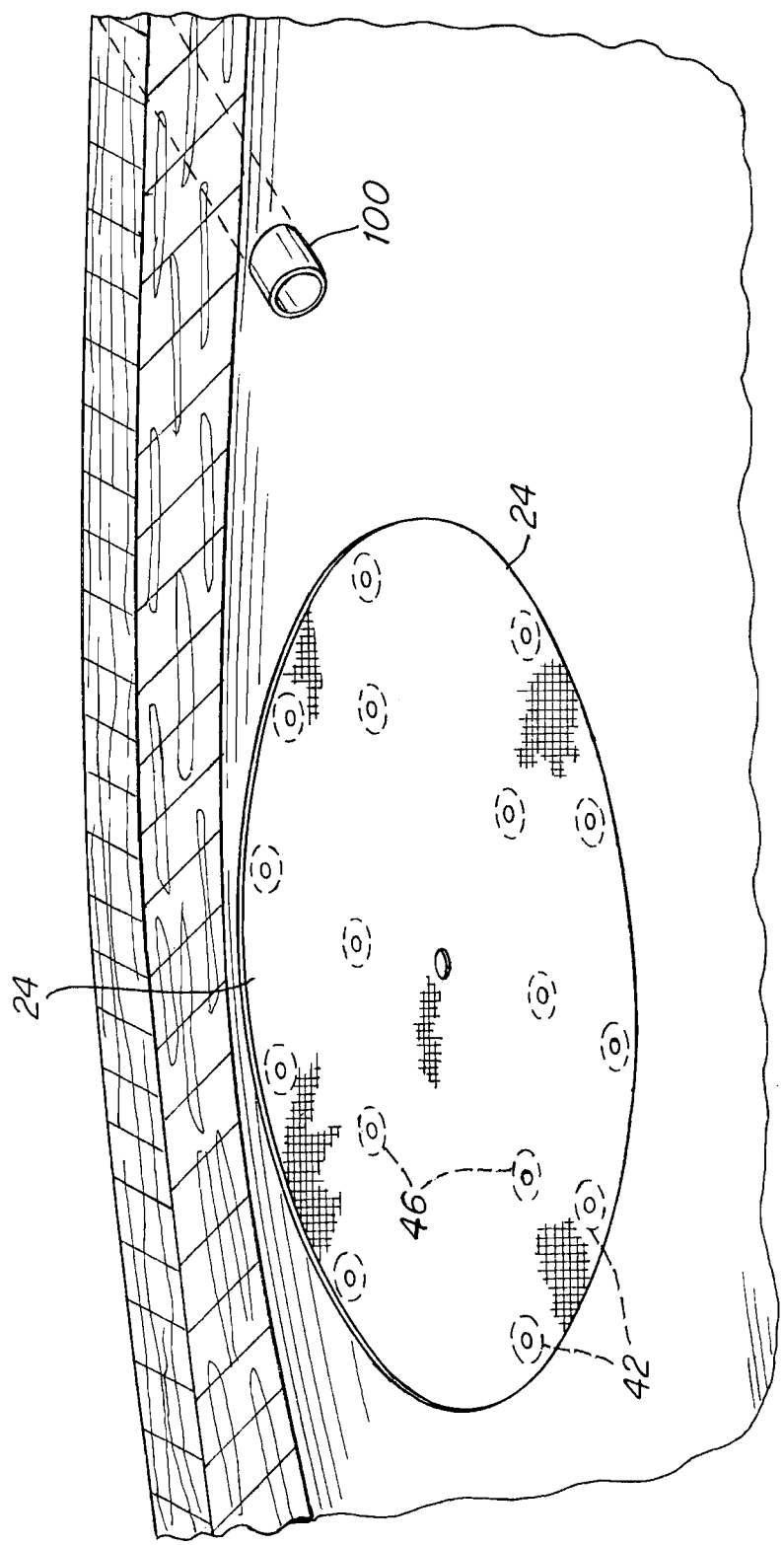

As shown in FIG. 12, the prosthetic patch 24 may be secured to the abdominal wall at various outer regions 42 and inner regions 46. However, as indicated above, the material delivery device may be configured to deliver material to any desired regions as should be apparent to one of skill.

In the method described above, the material delivery device is used to deliver a fixation material, such as an adhesive or other material for cross-linking, catalyzing or activating an otherwise inactive material component provided on the prosthesis, to a surface of the prosthesis and/or to one or more locations between the prosthesis and the tissue or muscle wall to attach the prosthesis to the tissue or muscle wall. Examples of adhesives that may be suitable for adhering a prosthesis to tissue using the material delivery device include, but are not limited to, cyanoacrylates (for example, DERMABOND available from Ethicon, INDERMIL available from Covidien, HISTOACRYL and HISTOACRYL BLUE available from Braun), albumin and glutaraldehyde (for example, BIOGLUE available from Cyrolife), fibrin glue (for example, TISSEEL available from Baxter, EVICEL available from Ethicon, VITAGEL available from Orthovita, CYROSEAL available from Thermogenesis), PEG based adhesive (for example, COSEAL available from Baxter, DURASEAL available from Covidien), and lysine derived urethane (for example, TISSUGLU available from Cohera).

For some procedures, in addition to or instead of the fixation material, the material delivery device may be used to deliver other materials, such as antibiotics, analgesics, growth factors and other therapeutic materials, as should be apparent to one of skill in the art. Such materials, if desired, may be delivered instead of, prior to, along with, or following delivery of the fixation material.

Figure 13:
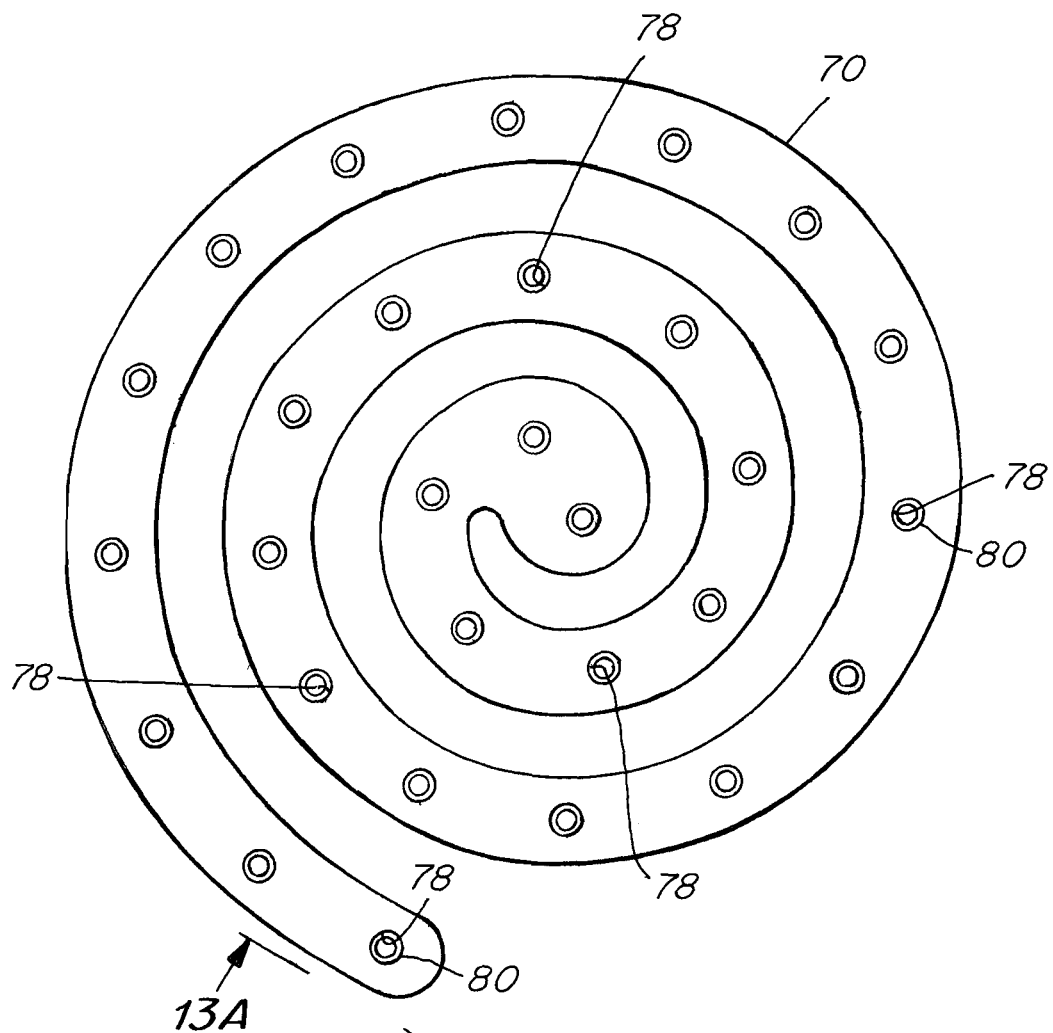
FIG. 13 is a schematic view of a prosthetic repair system having a spiral configuration according to another illustrative embodiment, with FIG. 13A being a schematic side view taken along view line 13A-13A of FIG. 13.
Figure 14:
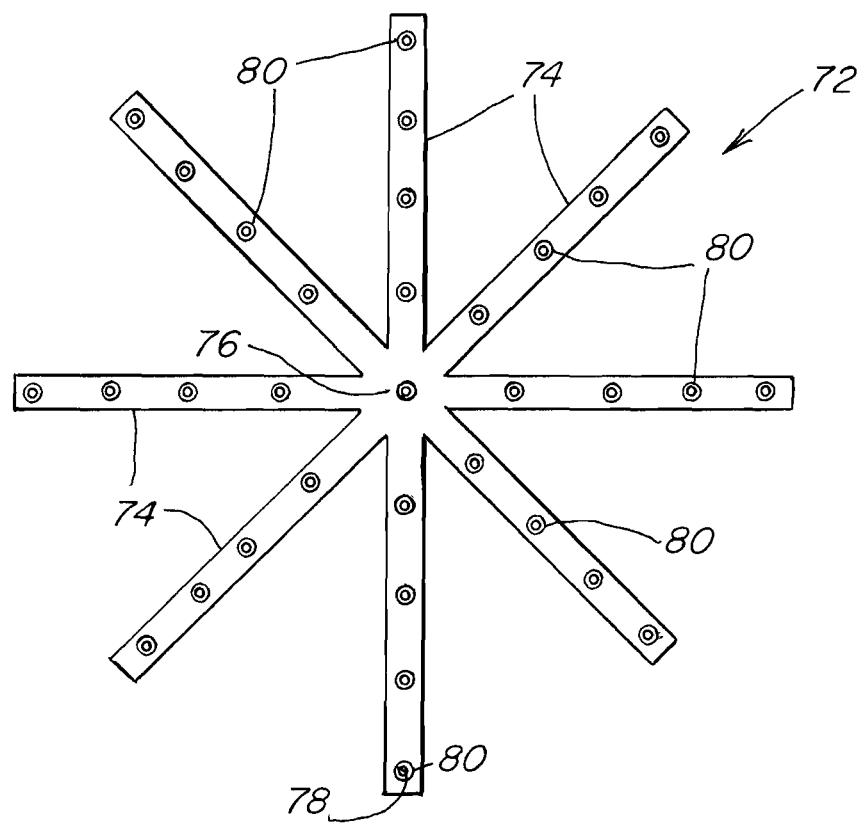
FIG. 14 is a schematic view of a prosthetic repair system having a spoke and hub configuration according to another illustrative embodiment.

As indicated above, other arrangements are contemplated for distributing material in any desired pattern or to any desired regions. In one illustrative embodiment as shown in FIG. 13, a manifold 70 may have a spiral configuration. In another illustrative embodiment as shown in FIG. 14, a manifold 72 may have a hub and spoke configuration that includes a plurality of spokes or arms 74 that extend in an outward radial direction from a hub or central region 76. As illustrated, delivery conduits or outlet ports 78 may be arranged on the manifold in any desired configuration, such as along the length of the spiral or the lengths of the spokes. An input conduit or port (not shown) may be provided at any portion of the manifold, such as the central region.

For some applications, it may be desirable to employ delivery conduits in the form of projections, such as nipples, that project or protrude from a surface of the manifold that faces and is placed against the prosthesis. The projections may be configured to penetrate through the thickness of the prosthesis for delivery of material. The projections may be arranged on the manifold in any desired pattern.

In one illustrative embodiment, the material delivery devices shown in FIGS. 13-14 include projections 80 located at and extending from the outlets 78 of the manifold.

Figure 13A:
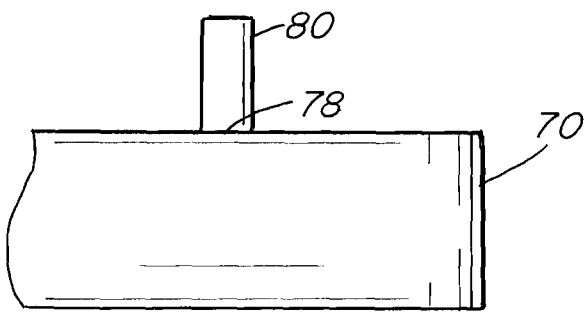

As shown in FIG. 13A, the projections 80 may extend perpendicular to the surface of the manifold and have sufficient length and stiffness or rigidity to penetrate at least partially or completely through the prosthesis in a pattern defined by the locations of the projections. If desired, the projections 80 may be tapered along its length or have a tapered tip to facilitate penetration of the prosthesis. The projections may be formed of any suitable biocompatible material, including plastics and metals, as should be apparent to one of skill in the art.

Figure 15:
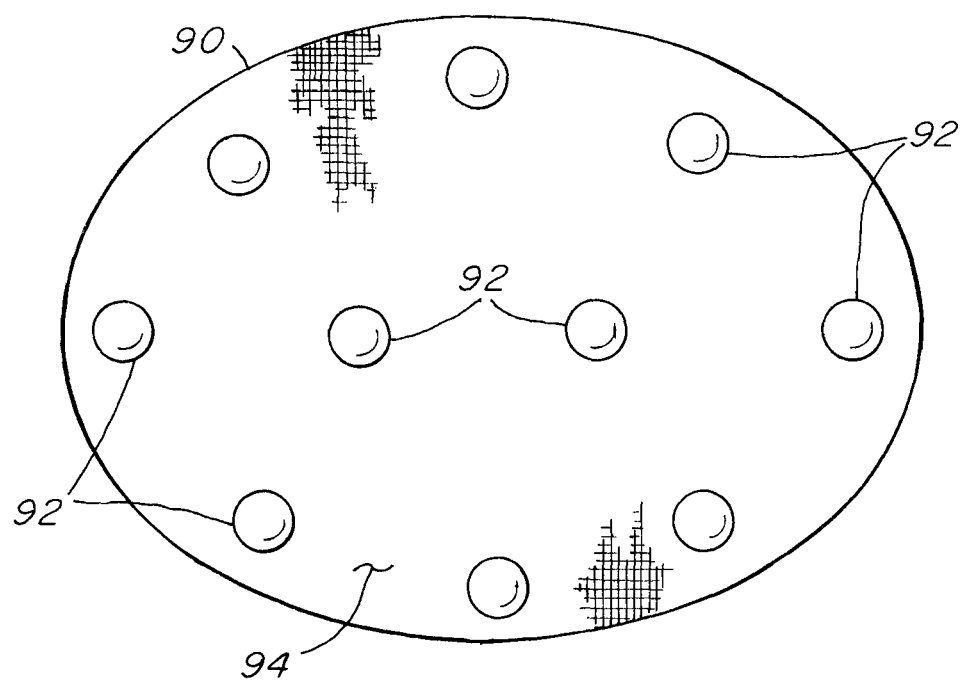
FIG. 15 is a schematic view of a prosthetic repair system for soft tissue or muscle wall repair with pre-filled reservoirs according to another illustrative embodiment.

For some procedures, it may be desirable to employ a material delivery system that is pre-loaded with material, such as a fixation material and/or other biocompatible materials, for delivery between a prosthesis and tissue. In one illustrative embodiment as shown in FIG. 15, a prosthesis 90 may include one or more reservoirs or capsules 92 that are pre-filled with an adhesive and/or other material. The reservoirs 92 are provided on the side 94 of the prosthesis that faces the tissue when implanted at a surgical site. The reservoirs may be configured to be selectively punctured, for example, using a suitable surgical tool, to release the adhesive on the tissue side of the prosthesis. Alternatively, the reservoirs may be formed of an absorbable material, such as a rapidly absorbable material, that break down or dissolve to release the adhesive and/or other material upon placement in the body. The reservoirs may have any suitable size and/or configuration and/or may be arranged in any suitable pattern as should be apparent to one of skill in the art.

For purposes of this patent application and any patent issuing thereon, the indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

The foregoing description of various embodiments are intended merely to be illustrative thereof and that other embodiments, modifications, and equivalents are within the scope of the invention recited in the claims appended hereto.

What is claimed is:

1. A prosthetic repair system, comprising:
   an implantable prosthesis for repairing a defect in a tissue or muscle wall, the prosthesis including first and second sides with a thickness therebetween; and
   a material delivery device configured to be coupled to the prosthesis, the material delivery device including:
   a manifold configured to be removably positioned adjacent the first side of the prosthesis, the manifold configured to receive material from a material source and distribute the material;

a plurality of delivery conduits fluidly coupled to the manifold, each of the plurality of delivery conduits including an inlet to receive material from the manifold and an outlet to deliver the material to a location adjacent the second side of the prosthesis, each of the plurality of delivery conduits configured to penetrate through the entire thickness of the prosthesis with the outlet located at or protruding beyond the second side of the prosthesis; and an input conduit fluidly coupled to the manifold to deliver the material thereto, the input conduit including an inlet to receive the material from the material source and an outlet to deliver the material to the manifold, the input conduit configured and arranged to penetrate through the prosthesis with the outlet coupled to the manifold on the first side of the prosthesis and the inlet extending beyond the second side of the prosthesis to deliver the material from the second side of the prosthesis to the manifold on the first side of the prosthesis.

2. The prosthetic repair system of claim 1, wherein the manifold is flexible.

3. The prosthetic repair system of claim 1, wherein each of the plurality of delivery conduits is flexible.

4. The prosthetic repair system of claim 1, wherein each of the plurality of delivery conduits includes a tube that extends from the manifold.

5. The prosthetic repair system of claim 1, wherein the input conduit has a length sufficient to be externally accessible from outside the patient.

6. The prosthetic repair system of claim 1, further comprising a support member configured to be coupled to the prosthesis, the support member constructed and arranged to unfurl the prosthesis from a reduced configuration for insertion into a patient into an expanded configuration for positioning at the defect.

7. The prosthetic repair system of claim 1, wherein the prosthesis includes a patch.

8. The prosthetic repair system of claim 7, wherein the first side is configured to be positioned facing away from the tissue or muscle wall and the second side is configured to be positioned facing toward the tissue or muscle wall.

9. The prosthetic repair system of claim 8, wherein the prosthesis includes an adhesion resistant barrier located on the first side and a mesh fabric located on the second side.

10. The prosthetic repair system of claim 1, wherein the material delivery device is coupled to the prosthesis, the manifold being removably supported adjacent the first side of the prosthesis, each of the plurality of delivery conduits penetrating through the entire thickness of the prosthesis with the outlet located at or protruding beyond the second side of the prosthesis, the input conduit penetrating through the prosthesis from the first side and extending beyond the second side by an amount greater than each of the plurality of delivery conduits.

11. The prosthetic repair system of claim 10, wherein each of the plurality of delivery conduits is removable from the prosthesis.

12. The prosthetic repair system of claim 10, wherein the prosthesis includes an outer periphery, the plurality of delivery conduits penetrating the prosthesis in proximity to the outer periphery.

13. The prosthetic repair system of claim 10, further comprising a support member coupled to the prosthesis, the support member constructed and arranged to unfurl the prosthesis from a reduced configuration for insertion into a patient into an expanded configuration for positioning at the defect.

14. The prosthetic repair system of claim 13, wherein the support member is removably supported adjacent the first side of the prosthesis.

15. The prosthetic repair system of claim 13, wherein the support member is inflatable to unfurl the prosthesis to the expanded configuration.

* * * * *

UNITED STATES PATENT AND TRADEMARK OFFICE
CERTIFICATE OF CORRECTION

PATENT NO. : 10,758,332 B2
APPLICATION NO. : 15/750536
DATED : September 1, 2020
INVENTOR(S) : Robert Richard et al.

Page 1 of 1

It is certified that error appears in the above-identified patent and that said Letters Patent is hereby corrected as shown below:

On the Title Page

Related U.S. Application Data should read:
(60) Provisional application No. 62/204,823, filed on Aug. 13, 2015.

Signed and Sealed this
Thirteenth Day of October, 2020

Andrei Iancu
*Director of the United States Patent and Trademark Office*